United States Patent

Schmidt et al.

[11] Patent Number: 6,156,527
[45] Date of Patent: Dec. 5, 2000

[54] CHARACTERIZING POLYPEPTIDES

[75] Inventors: Günter Schmidt, Cambridge; Andrew Hugin Thompson, Ayr, both of United Kingdom

[73] Assignee: Brax Group Limited, United Kingdom

[21] Appl. No.: 09/341,993

[22] PCT Filed: Jan. 23, 1998

[86] PCT No.: PCT/GB98/00201

§ 371 Date: Sep. 10, 1999

§ 102(e) Date: Sep. 10, 1999

[87] PCT Pub. No.: WO98/32876

PCT Pub. Date: Jul. 30, 1998

[30] Foreign Application Priority Data

Jan. 23, 1997 [GB] United Kingdom .................. 9701357
Dec. 19, 1997 [GB] United Kingdom .................. 9726947

[51] Int. Cl.[7] .............................. C12Q 1/37; C12Q 1/00; C12Q 1/34
[52] U.S. Cl. .................... 435/24; 435/18; 435/4; 435/23
[58] Field of Search ..................... 435/24, 18, 4, 435/23

[56] References Cited

FOREIGN PATENT DOCUMENTS

| 0 306 610 | 3/1989 | European Pat. Off. . |
| 0 594 164 | 4/1994 | European Pat. Off. . |
| 2 269 177 | 2/1994 | United Kingdom . |
| WO 90/05192 | 5/1990 | WIPO . |

OTHER PUBLICATIONS

Pauly et al, J. Biological Chemistry, vol. 271 (38), p. 23222, (Abstract Only) Sep. 1996.
Seielstad et al., Biochemistry (1995), 34(39), 12605–12615, XP002063749.
Debrabant et al., Mol. biochem. Parasitol. (1992), 53(1–2) pp. 89–95, XP002063750.
Mareya et al., Bioorg. Med. Chem. (1995), 3(5), pp. 525–532, XP002063751.
Muir et al., Biology, vol. 3, No. 10, Oct. 1996, pp. 817–825, XP002063752.

*Primary Examiner*—Louise N. Leary
*Attorney, Agent, or Firm*—Burns, Doane, Swecker & Mathis LLP

[57] ABSTRACT

A method for characterizing polypeptides, which comprises: (a) treating a sample comprising a population of one or more polypeptides with a cleavage agent which is known to recognize a specific amino acid residue or sequence in polypeptide chains and to cleave at a cleavage site, whereby the population is cleaved to generate peptide fragments; (b) isolating a population of the peptide fragments which bear at one end a reference terminus comprising either only a C-terminus or only an N-terminus and which bear at the other end the cleavage site proximal to the reference terminus; and c) determining a signature sequence of at least some of the isolated fragments, which signature sequence is the sequence of a predetermined number of amino acid residues running from the cleavage site; wherein the signature sequence and the relative position of the cleavage site to the reference terminus characterize the polypeptide or each polypeptide.

16 Claims, 11 Drawing Sheets

Step 4 ↓

↓ Step 5

↓ Step 6

Step 7

Step 5

Step 6

Step 7

CHARACTERIZING POLYPEPTIDES

FIELD OF THE INVENTION

The present invention relates to a method for characterizing polypeptides and to methods for identifying and assaying such polypeptides.

BACKGROUND TO THE INVENTION

The characterisation and identification of polypeptides from complex mixtures thereof, such as protein samples found in biological systems, is a well-known problem in biochemistry. Traditional methods involve a variety of liquid phase fractionation and chromatography steps followed by characterization, for example by two dimensional gel electrophoresis. Such methods are prone to artefacts and are inherently slow. Moreover, automation of such methods is extremely difficult.

Patent Application PCT/GB97/02403, filed on Sep. 5, 1997, describes a method for profiling a cDNA population in order to generate a 'signature' for every cDNA in the population. It is assumed in that method that a short sequence of about 8 bp that is determined with respect to a fixed reference point is sufficient to identify almost all genes. This system relies on immobilizing the cDNA population at the 3' terminus and cleaving it with a restriction endonuclease. This leaves a population of 3' restriction fragments. The patent describes a technique that allows one to determine a signature of roughly 8 to 10 base pairs at a specified number of bases from the restriction site which is a sufficient signature to identify nearly all genes.

Techniques for profiling proteins, that is to say cataloguing the identities and quantities of proteins in a tissue, are less well developed in terms of automation or high throughput. The classical method of profiling a population of proteins is by two-dimensional electrophoresis. In this method a protein sample extracted from a biological sample is separated on a narrow gel strip. This first separation usually separates proteins on the basis of their iso-electric point. The entire gel strip is then laid against one edge of a rectangular gel. The separated proteins in the strip are then electrophoretically separated in the second gel on the basis of their size. This technology is slow and very difficult to automate. It is also relatively insensitive in its simplest incarnations. A number of improvements have been made to increase resolution of proteins by 2-D gel electrophoresis and to improve the sensitivity of the system. One method to improve the sensitivity of 2-D gel electrophoresis and its resolution is to analyse the protein in specific spots on the gel by mass spectrometry. One such method is in-gel tryptic digestion followed by analysis of the tryptic fragments by mass spectrometry to generate a peptide mass fingerprint. If sequence information is required, tandem mass spectrometry analysis can be performed.

More recently attempts have been made to exploit mass spectrometry to analyze whole proteins that have been fractionated by liquid chromatography or capillary electrophoresis. In-line systems exploiting capillary electrophoresis mass spectrometry have been tested. The analysis of whole proteins by mass spectrometry, however, suffers from a number of difficulties. The first difficulty is the analysis of the complex mass spectra resulting from multiple ionisation states accessible by individual proteins. The second major disadvantage is that the mass resolution of mass spectrometers is at present quite poor for high molecular weight species, i.e. for ions that are greater than about 4 kilodaltons in mass so resolving proteins that are close in mass is difficult. A third disadvantage is that further analysis of whole proteins by tandem mass spectrometry is difficult as the fragmentation patterns for whole proteins are extremely complex.

SUMMARY OF THE INVENTION

The present invention provides a method for characterising polypeptides, which comprises:

(a) treating a sample comprising a population of one or more polypeptides with a cleavage agent which is known to recognise in polypeptide chains a specific amino acid residue or sequence and to cleave at a cleavage site, whereby the population is cleaved to generate peptide fragments;

(b) isolating a population of the peptide fragments which bear at one end a reference terminus comprising either only a C-terminus or only an N-terminus and which bear at the other end the cleavage site proximal to the reference terminus; and (c) determining a signature sequence of at least some of the isolated fragments, which signature sequence is the sequence of a predetermined number of amino acid residues running from the cleavage site;

wherein the signature sequence and the relative position of the cleavage site to the reference terminus characterise the or each polypeptide.

The invention therefore describes a system analogous to that of PCT/GB97/02403, but for use with proteins. Since there are 20 monomers that make up a protein there are a great many more possible variants at a particular site in a sequence and so the length of signature required from a protein sequence is much shorter than that required from a cDNA sequence to identify it uniquely.

This invention can use liquid phase separation techniques and mass spectrometry to resolve proteins and protein fragments to facilitate automation and avoid the artefacts and inherent slowness and lack of automation in gel based techniques such as 2-D gel electrophoresis.

The reference terminus may be attached to a solid phase support to immobilize the population of polypeptides or peptide fragments thereof. Preferably, the population of polypeptide is immobilised before treatment with the cleavage agent. In this way, the peptide fragments produced on treatment with the cleavage agent remain immobilized and can be readily isolated by washing away unwanted material present in the liquid phase. The solid phase support may comprise suitable beads or other such supports well known in this art. Such supports or substrates may be chosen to bind selectively to either the N-terminus or the C-terminus and this is discussed in further detail below.

In one embodiment, the reference terminus is attached to the solid phase support by: (i) treating the polypeptides with a blocking agent to block all exposed reference groups, which comprise either carboxyl groups or primary amine groups; (ii) cleaving the reference terminal amino acids to expose unblocked reference termini; and (iii) treating the unblocked reference termini with an immobilization agent capable of coupling to the solid phase support; wherein step (b) comprises binding the treated reference termini to the solid phase support and removing unbound peptide fragments. In an alternative embodiment, the method further comprises (i) preparing the sample step (a) by pre-treating the polypeptides with a blocking agent to block all exposed reference groups, which comprise either carboxyl groups or primary amine groups, so that subsequent treatment of the sample with the cleavage agent generates peptide fragments bearing unblocked reference termini; (ii) biotinylating the unblocked reference termini; and (iii) binding the peptide fragments containing the unblocked reference termini to a solid phase support; wherein step (b) comprises eluting unbound peptide fragments therefrom. Preferably, the immobilisation agent comprises a biotinylation agent.

The cleavage agent must recognize a specific amino acid residue or sequence of amino acids reliably. The cleavage site may be at the specific amino acid residue or sequence or at a known displacement therefrom. The cleavage agent may be a chemical cleavage agent such as cyanogen bromide. Preferably, the cleavage agent is a peptidase, such as a serine protease, preferably trypsin.

As discussed in further detail below, depending on the number of proteins or polypeptides in a given sample, it may be advantageous to sort the polypeptides into manageable sub-populations. Sorting can be effected before treatment of the sample with the cleavage agent or after cleavage. As discussed in further detail below, the sample of step (a) may comprise a sub-cellular fraction. In this way, the method further comprises a step of sub-cellular fractionation before step (a). The sample of step (a) may be prepared by liquid chromatography of either a crude fraction or a sub-cellular fraction. A preferred method of determining the signature sequence is by mass spectrometry and this may be preceded by a high pressure liquid chromatography step to resolve the peptide fragments. Alternatively, the peptide fragments may be subjected to ion exchange chromatography before step (c), followed by sequencing by either mass spectrometry or other methods.

In accordance with the method of the present invention, the predetermined number of amino acid residues required to constitute the signature sequence will vary according to the size of the polypeptide population. Preferably, the predetermined number of amino acid residues is from 3 to 30, more preferably 3 to 6.

The present invention further provides a method for identifying polypeptides in a test sample. The method comprises characterizing the polypeptides as described above and comparing the signature sequences and relative positions of the cleavage site obtained thereby with the signature sequences and relative positions of the cleavage site of known polypeptides in order to identify the or each polypeptide in the test sample. This method can be used to identify a single unknown polypeptide or a population of unknown polypeptides by comparing their characteristics (i.e. their signature sequences and relative positions of cleavage site) with those of previously identified polypeptides. It is envisaged that the database of such characteristic can readily be compiled.

In a further aspect, the present invention provides a method for assaying for one or more specific polypeptides in a test sample. The method comprises performing a method as described above, wherein the cleavage agent and relative position of the cleavage site is predetermined and the signature sequence is determined in step (c) by assaying for a predetermined sequence of amino acid residues running from the cleavage site. Preferably, the cleavage site and signature sequence are predetermined by selecting corresponding sequences from one or more known target polypeptides, such as those available from the database.

BRIEF DESCRIPTION OF THE DRAWINGS

The invention will now be described in further detail, by way of example only, with reference to the accompanying drawings, in which.

BRIEF DESCRIPTION OF THE INVENTION

Protein Signatures

Figure 1A:
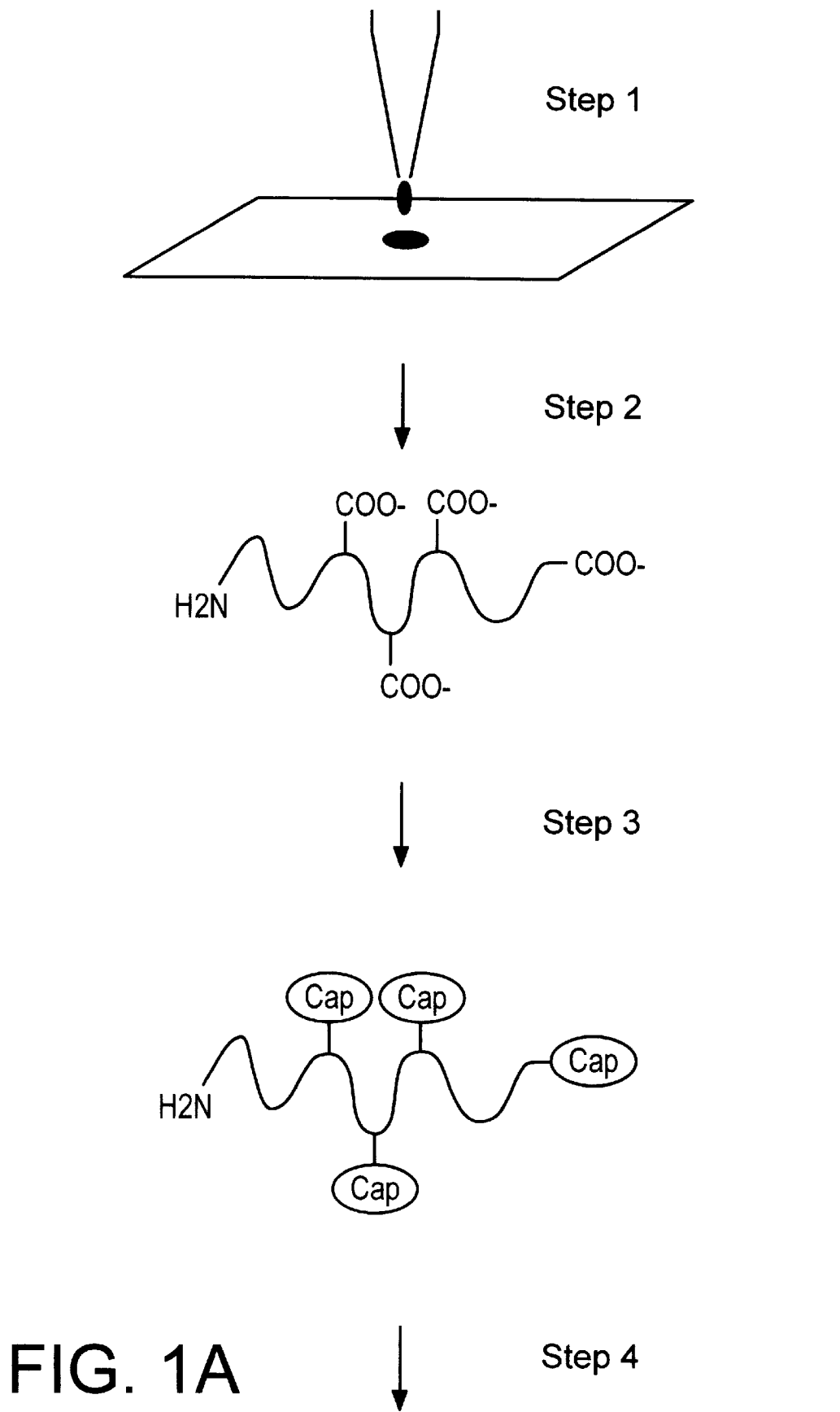
FIGS. 1A-1C shows a reaction scheme according to one embodiment of the invention.

The essence of this system is that one can immobilize a population of proteins onto a solid phase substrate at one terminus of the molecule. Proteins are directional so a particular terminus can be chosen in a manner dependent on the chemistry of the immobilization agent, for example the Edman reagent (phenyl isothiocyanate) can be used selectively to remove amino acids from the N-terminus of a protein; however, if phenyl isocyanate is used the N-terminus is simply capped. A derivative of this molecule that could be coupled to a cleavable linker on a solid-phase substrate would allow a protein to be immobilized at its N-terminus and subsequently removed by cleavage of the linker. During peptide synthesis, the C-terminus is usually immobilized as a benzyl ester, through the use of a chloromethyl group. Such chemistry may be adapted to immobilize proteins at this terminus, if desired.

A population of immobilized proteins is then treated with a sequence specific peptidase such as trypsin to leave a population of N-terminal cleavage fragments. Such fragments can be considered to be analogous to an expressed sequence tag for a protein. One can then sequence the resultant peptide signatures by mass spectrometry. Terminal fragments are most meaningful, in that the position of all resultant peptide in the protein is known and the termini are usually accessible at the surface of most proteins.

Sorting Proteins

Obviously a population of proteins extracted from a cell is going to be a significant number of distinct species. If, as it is thought there are roughly 15000 genes expressed in the average human cell, one can expect as many proteins. Clearly one cannot sequence all of these by mass spectrometry in a single step, with present technology. For this reason a protein population of such size needs to be sorted into manageable sub-sets.

A generalized system for profiling proteins must attempt to resolve a protein population into reasonable discrete subsets of relatively uniform size. This is most readily achieved by separation on the basis of global properties of proteins, that vary over a broad and continuous range, such as size and surface charge, which are the properties used most effectively in 2-D gel electrophoresis. Such separations can be achieved as rapidly or more so using liquid chromatographic techniques. In fact, by following one liquid chromatography separation by another, one can resolve proteins in as many dimensions as one requires, since there is a great deal more flexibility in liquid chromatography separation systems, although one would ideally avoid too many separation steps to prevent sample loss.

Sorting can be effected during extraction, after extraction of proteins from their source tissue or after cleavage of immobilized peptides.

Sorting during cell fractionation

Proteins are intrinsically sorted in vivo, in terms of their compartmentalization within a cell. Various techniques are available that allow one to sort proteins on the basis of their cellular compartments. Fractionation protocols involve various cell lysis techniques such as sonication, detergents or mechanical cell lysis that can be coupled to a variety of fractionation techniques, mainly centrifugation. Separation into membrane proteins, cytosolic proteins and the major membrane bound sub-cellular compartments, such as the nucleus and mitochondria, is standard practice. Thus one can effectively ignore certain classes of protein if one chooses, e.g. mitochondrial proteins are likely to be uninteresting in a lot of cases. Membrane, cytosolic and nuclear compartments will be of particular interest on the whole.

Sorting after extraction

Since proteins are highly heterogenous molecules numerous techniques for separation of proteins are available on the basis of size, hydrophobicity, surface charge and various combinations of the above using liquid chromatography in its various incarnations. Separation is effected by an assortment of solid phase matrices derivitised with various functionalities that adhere to and hence slow down the flow of proteins through the column on the basis of the properties above. Molecules are normally loaded into such columns in conditions favouring adhesion to the solid phase matrix and selectively washed off in steadily increasing quantities of a second buffer favouring elution. In this way the proteins with the weakest interactions with a given matrix elute first.

Various formats for liquid chromatography exist but for greatest speed of throughput and for the most discrete separations High Pressure Liquid Chromatography (HPLC) formats are favoured. In this format the matrix is designed to be highly incompressible and when derivitized allow chromatographic separation to be performed at extremely high pressures which favours rapid and discrete separation.

Sorting of cleaved peptides

Liquid chromatography mass spectrometry (LCMS) is a well developed field. HPLS systems directly coupled to electrospray mass spectrometers are in widespread use. HPLC is a fast and effective way of resolving peptides after they have been cleaved from their immobilized state.

Alternatively sorting peptides by ion exchange chromatography might be advantageous, in that short peptides could be separated in an almost sequence dependent manner: the amino acids that are ionizable have known pKa values and hence elution of peptides from such a column at a specific pH, would be indicative of the presence of particular amino acids in that sequence. For example, aspartate residues have a pKa of 3.9 and glutamate residues 4.3. Elution of a peptide at pH 4.3 would be indicative of the presence of glutamate in the peptide. These effects are sometimes masked in large proteins but should be distinct in short peptide, hence would be extremely useful as sorting features.

Combination of the above techniques will allow various sorting protocols to be developed that will allow great control over the form of the protein profile generated. In this way, identification of most proteins expressed in a cell should be achievable.

Sequencing of peptides by mass spectrometry

Peptides can be readily sequenced directly by tandem mass spectrometry. In general, peptide mixtures are injected into the mass spectrometer by electrospray, which leaves them in the vapour phase. The first mass spectrometer acts as a filter selecting molecules to enter the second mass spectrometer on the basis of their mass charge ratio, such that essentially only a single species enters the second mass spectrometer at a time. On leaving the first mass spectrometer, the selected peptide passes through a collision chamber, which results in fragmentation of the peptide. Since fragmentation occurs mostly at the peptide bond, the pattern of fragments corresponds to a series of subspecies of peptides and amino acids that compose the original peptide. The distinct pattern of masses of single amino acids, 2-mers, 3-mers, etc. generated in the fragmentation of the peptide is sufficient to identify its sequence.

The end result is then that a population of proteins can be arbitrarily sorted into populations of peptides of convenient size to be fed into an electrospray tandem mass spectrometer for direct sequencing. Completion of such an analysis for an entire cell's proteins would give a profile of what proteins are present and in what relative quantities. Absolute quantitation could be achieved by 'spiking' a protein population with known quantities of particular proteins, known to be absent, e.g. plant proteins in animal samples or visa versa against which to calibrate results.

Protein Signatures

This invention provides a method of capturing a population of proteins onto a solid phase substrate by one terminus of each protein in the population. This invention also provides a method of cleaving proteins that have been derivatized at one terminus with an agent that can be used to immobilise that terminus on a solid phase substrate. This allows a single peptide for each protein in a population to be captured onto a solid phase substrate thus peptides from the chosen terminus can be separated from other peptides generated by the cleavage step and can be isolated. This invention also provides a method to allow all the peptides generated in a cleavage step that are not from the reference terminus to be captured leaving a single terminal peptide per protein free in solution for analysis.

A population of peptides generated according to the methods of this invention can be analysed in a number of ways preferably by mass spectrometry.

Two forms of analysis are preferred. The first is to determine peptide mass fingerprints for the population of signature peptides generated. In this method the mass of each peptide, preferably the accurate mass, is determined. A significant proportion of signature peptides should be uniquely identified by this form of analysis. Any mass peaks that are unknown can be further characterised by the second form of preferred analysis. Ions of a specific mass can be selected for collision induced dissociation in a tandem mass spectrometer. This technique can be used to determine sequence information for a peptide.

Capturing Peptides

This invention provides methods that exploit derivitization of proteins with various agents, including existing peptide sequencing reagents, to isolate a single 'signature' peptide from each member of a population of proteins. This invention may be practiced in two formats. The methods of this invention allow a reference terminus to be selected from the proteins in a population. In the first format this reference terminus may be derivatized with an immobilization agent. If the proteins derivatized in this manner are treated with a sequence specific cleavage agent to generate peptides, the peptides from the reference termini of the proteins in a mixture can be specifically captured leaving the remaining peptides free in solution. This first format is discussed in the following section headed "Format 1". In the second format a single peptide sample per protein is generated by capturing the peptide fragments that are not from the chosen reference terminus, thus leaving the signature peptides free in solution.

Format 1

Figure 3A:
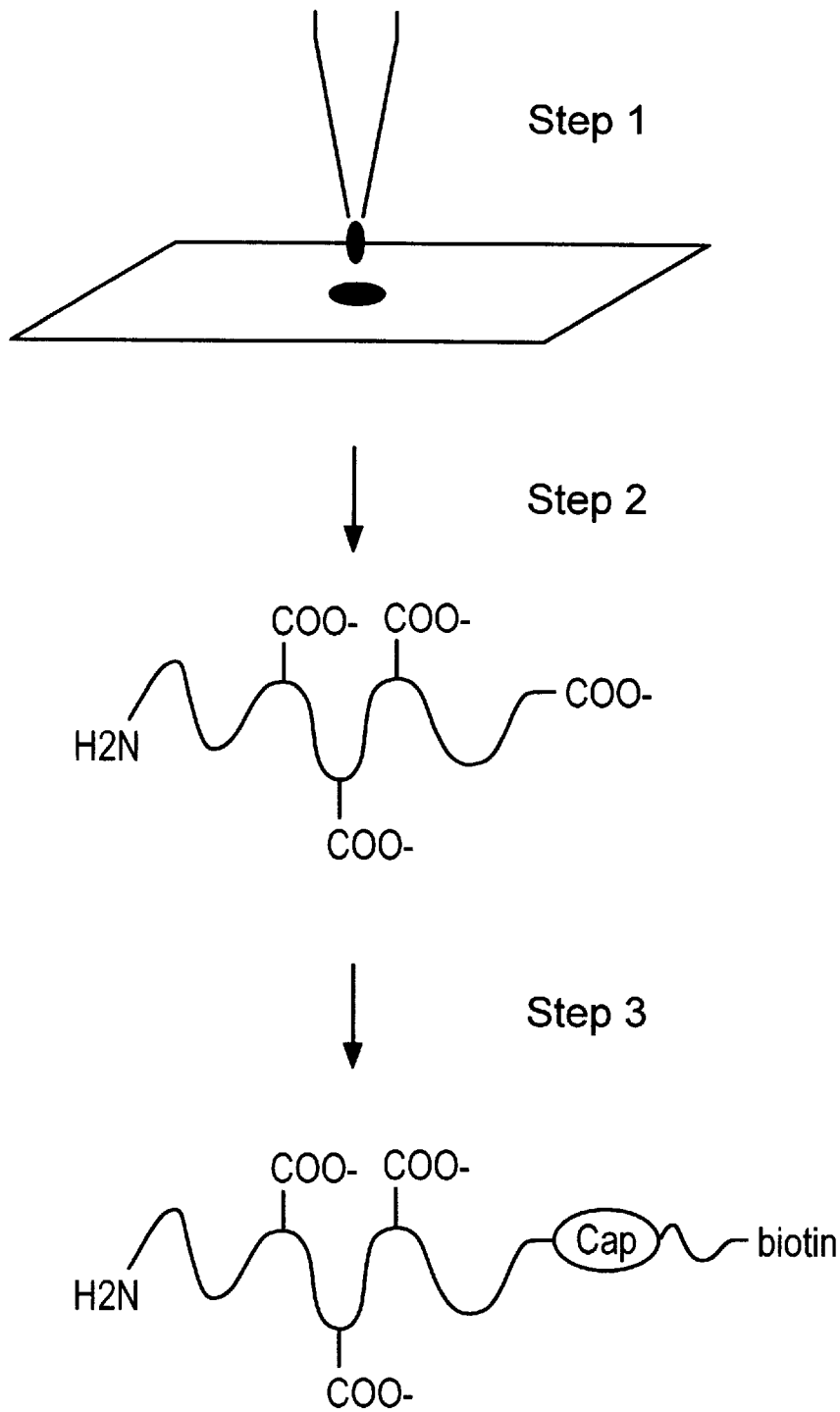
FIGS. 3A-3B shows a reaction scheme according to a simple embodiment of the invention.
Figure 3B:
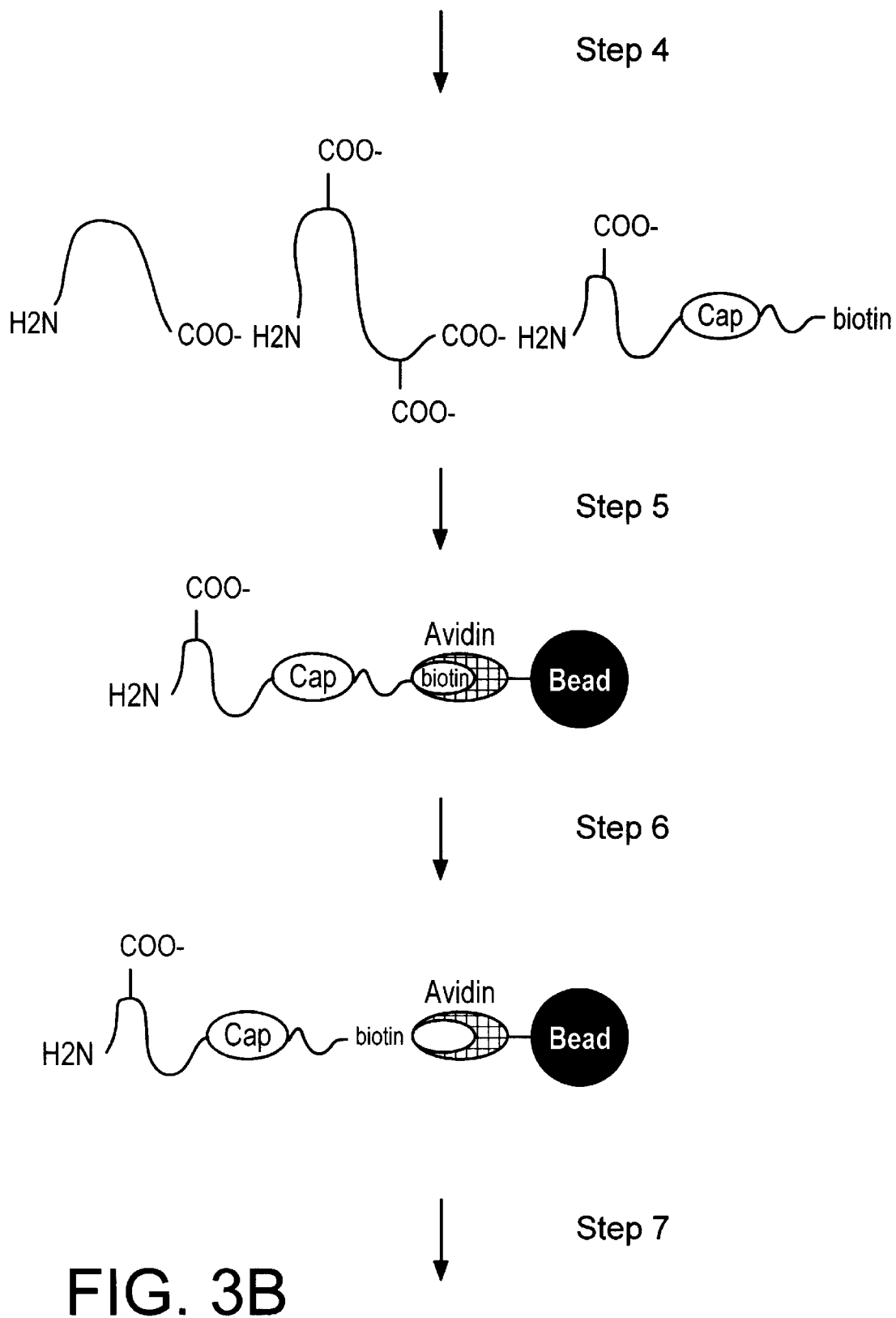
Figure 4A:
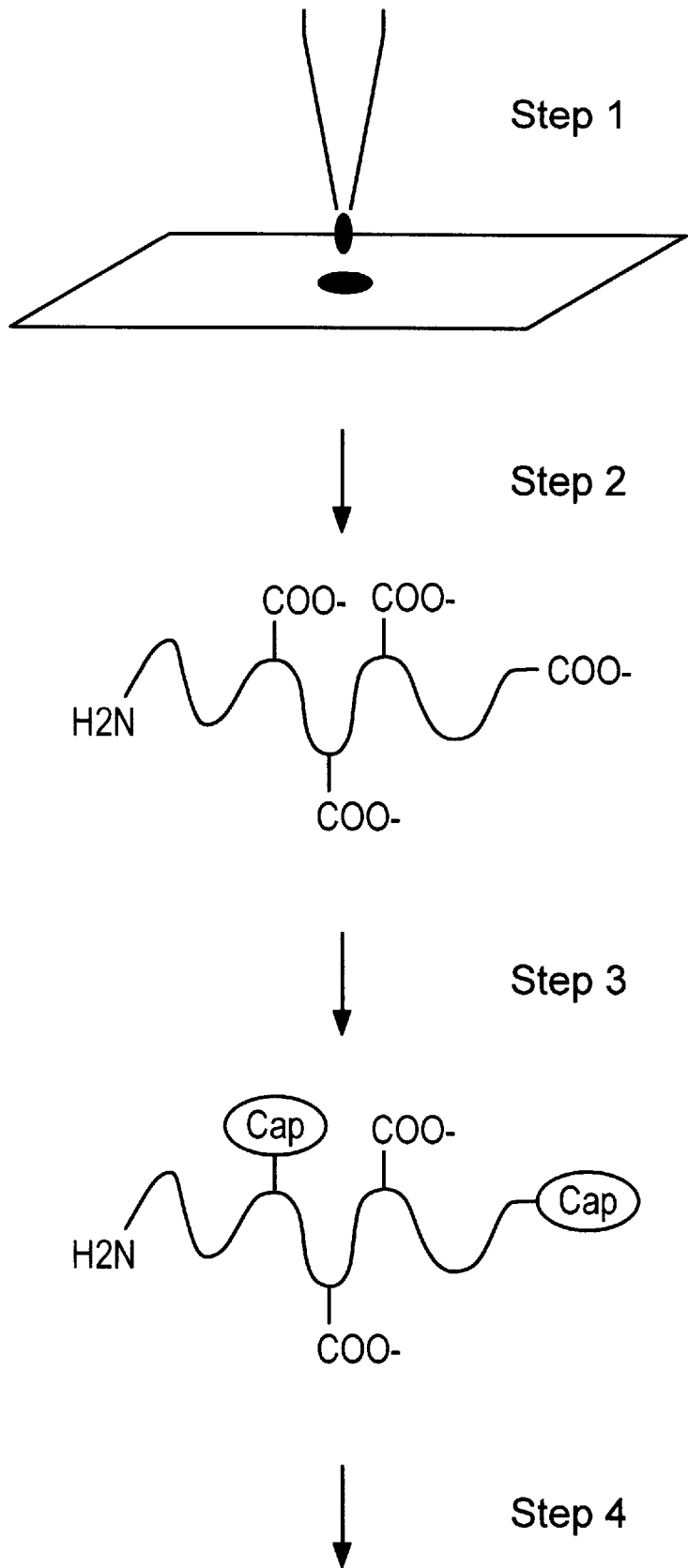
FIGS. 4A-4C shows a reaction scheme according to a variation of the embodiment shown in FIG. 1.
Figure 4B:
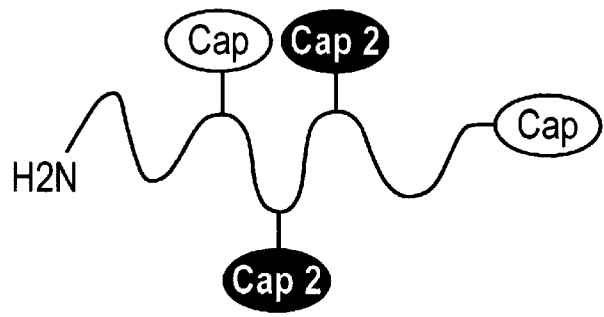
Figure 4B:
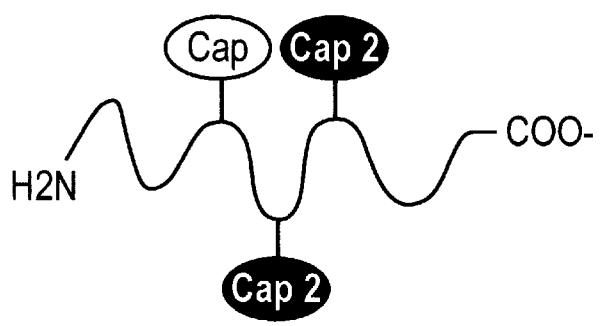
Figure 4B:
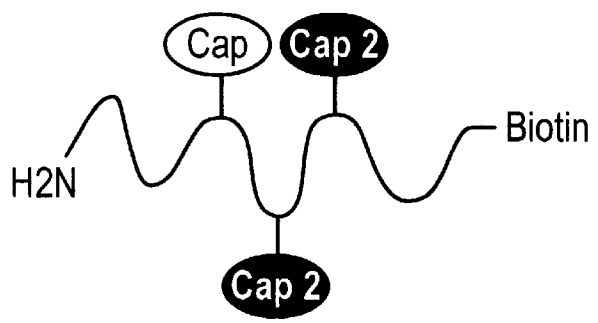
Figure 4C:
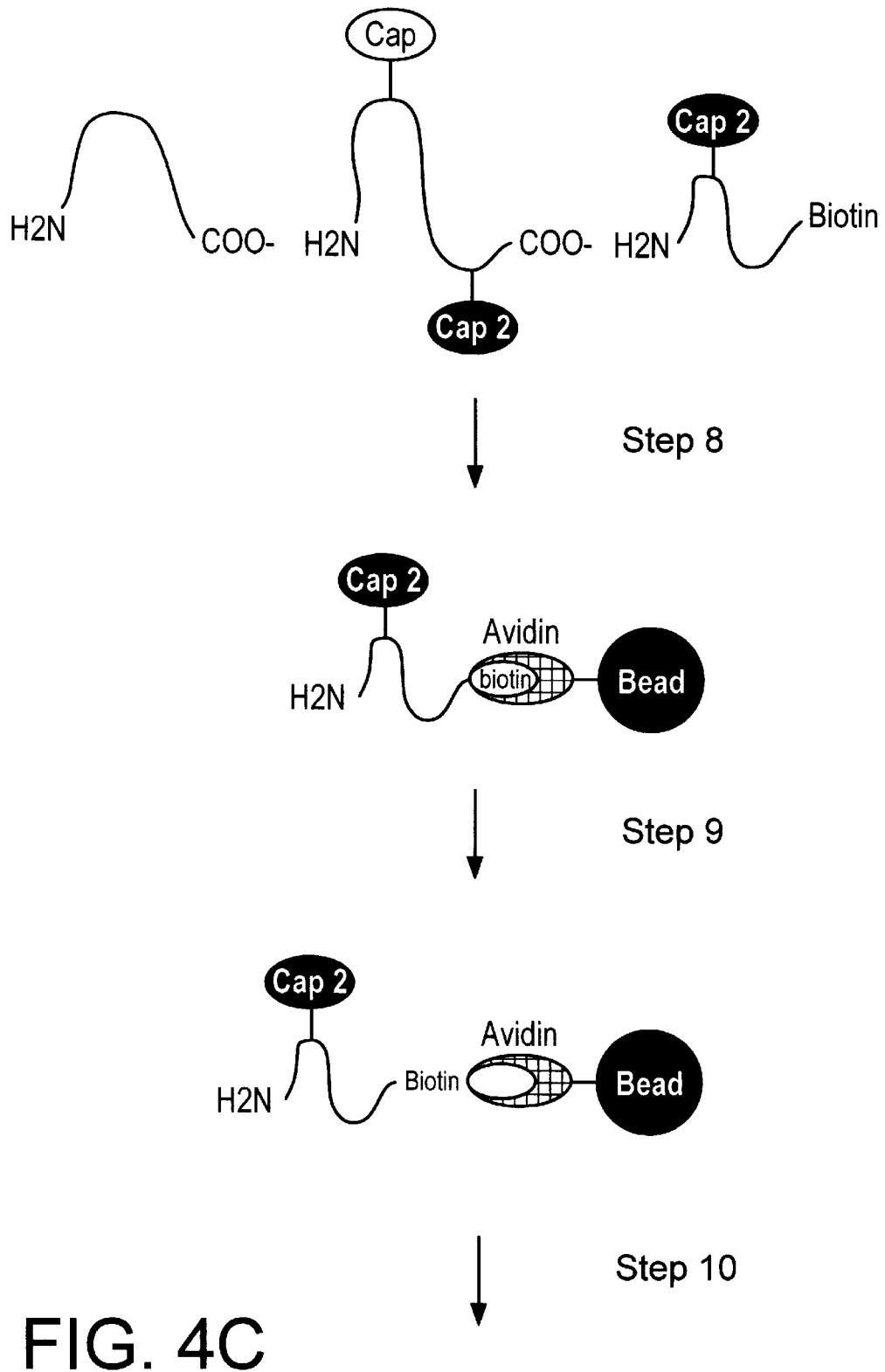

In the simplest embodiment of this invention as shown schematically in FIG. 3, a population of proteins is reacted with a modified sequencing agent specific for one terminus of each protein in the population. The modified sequencing agent carries an immobilization agent in order that proteins derivatised with the sequencing agent may be captured onto a solid phase support. The captured proteins may then be cleaved with a sequence specific cleavage agent. This cleavage step will generate a series of peptide fragments in solution and will leave a single peptide protein captured on the solid phase support. The peptides free in solution are then washed away. The immobilized peptides can then be released from the solid phase support by completing the sequencing reaction for the coupled terminal amino acid. The Edman reagent (phenyl isothiocyanate) could be modified to carry an immobilization agent, the phenyl ring could be substituted with a group linked to an appropriate immobilisation effector such as biotin. A population of proteins derivatised with this reagent could be cleaved with trypsin. The derivatised terminal peptides could then be immobilized on an avidinated solid phase support allowing underivatized peptides to be washed away. The peptides could then be released from the solid phase support by disrupting the avidin-biotin reaction. This will leave N-terminal peptides free in solution. These peptides can then be analysed by mass spectrometry. It may be desirable to fractionate the peptide prior to mass spectrometry but this fractionation step is optional. Alternatively a modified C-terminal sequencing agent might be used to capture proteins by the C-terminus. The C-terminus is generally not post-translationally modified and so may be the preferred terminus to capture a population of proteins. Further embodiments of this invention are discussed below.

C-terminal sequencing agents:

Unmodified C-terminal sequencing agents can be used to generate a signature peptide. A further embodiment of the present invention is as follows and is described schematically in FIG. 1. In the first step a protein population extracted from a tissue is loosely immobilized onto a membrane, such as a PVDF membrane. The solvents used to extract proteins from a tissue sample are generally very harsh, usually containing agents such as urea, thiourea and detergents, since proteins have widely varying solubilities. Immobilizing extracted proteins onto a membrane allows them to be washed with other solvents prior to modification. The protein population, thus captured, is then derivatised with a coupling agent, such as diphenyl phosphoroisothiocyanatidate from Hewlett-Packard, (Miller et al., Techniques in Protein Chemistry VI 219–227) in a method that is essentially the same as that which one would use for a normal sequencing reaction for a single protein giving peptidylacylisothiocyanates for all proteins. The coupling reagent also reacts with other free carboxyl groups also giving acylisothiocyanate derivatives. The coupling agent may, however, react incompletely with some carboxylic acid side chains. It may, therefore, be desirable to perform additional derivatisation steps using more reactive reagents to ensure that all free carboxyl groups are derivatised. This variation is shown in FIG. 4. The derivatized protein population is then treated with pyridine to effecting ring closure of the terminal acylisothiocyanate derivative. One can then cleave the C-terminal residue by addition of a cleavage agent such as trimethylsilanolate, from Hewlett-Packard, which cleaves the terminal amino acid from each protein releasing the thiohydantoin-amino acid derivative of the terminal amino acid. This exposes a free carboxyl at the penultimate residue of each protein. This can be specifically derivatized with biotin using 5-(biotimamido)pentylamine since all other carboxyl groups are derivatized. In this way all the proteins in a population can be derivatised at the C-terminal with biotin. The biotinylated population, still on the PVDF membrane is then treated with an appropriate sequence specific cleavage agent. Trypsin is generally used for mass spectrometry application as this generally leaves the N-terminal side of the cleavage site protonated which is desirable. Trypsin specifically cleaves adjacent to basic residues. If an enzyme is used the immobilized peptides would have to be washed with some form of physiological buffer to allow trypsin to function. This will leave a population of cleaved peptides, some of which are biotinylated which can be desorbed from the PVDF membrane into solution. The biotinylated peptides can be captured using a solid phase matrix derivatized with monomeric avidin. Non-immobilized peptides can then be washed away, leaving an immobilized population of C-terminal peptides which comprise the tag used to identify proteins in a population. After washing away free peptides, the immobilised tags can be released from the solid phase support by addition of acid which disrupts the biotin/avidin interaction—monomeric avidin is best for this purpose. In an alternative embodiment the biotinylated peptides can be captured on an avidinated support prior to sequence specific cleavage.

N-terminal sequencing agents:

N-termini of a large proportion of cellular proteins are blocked. For the purposes of profiling those proteins whose N-termini are not blocked one can use the corresponding N-terminal sequencing agents to derivatize amino groups including the terminal amino group. The terminal amino acid can be cleaved and the newly exposed amine at the penultimate amino acid can be derivatised with an immobilization agent. The biotinylated proteins can then be cleaved and the terminal signature peptides can be captured and analyzed. This would however be limited to those N-termini that are not already blocked.

Format 2

This method is shown schematically in FIG. 2. In this method a reagent that derivatizes carboxyl residues is used to cap all carboxyl residues including the C-terminal carboxyl group in the protein population of interest. The protein population is then cleaved with trypsin or another sequence specific cleavage reagent that cleaves at the peptide bond to generate an amino and carboxyl group on the C-terminal fragments respectively. At this stage all peptides except the terminal peptides, which are capped will have a free carboxyl. These free carboxyls can be derivatized with 5-(biotinamido)pentylamine or some other immobilization agent. If biotin is used then one can capture all the biotinylated non C-terminal peptides onto a solid phase matrix derivatized with avidin. An avidinated affinity column in-line with a mass spectrometer would allow C-terminal peptides to be selectively eluted directly into the mass spectrometer for anaylsis.

This technique is equally applicable to generating peptide tags from the N-terminus of a population of proteins. Reagents which derivatize amine groups can be used to selectively cap all amine groups on a protein including the N-terminal amine group. Cleavage will expose amines in non-terminal peptides which can be derivatized with biotin allowing selective capture of non N-terminal peptides. This is important since many proteins are modified at the N-terminus and the N-terminal amine is often inaccessible to reagents. Thus selectively capturing non N-terminal peptides is a means of generating a signature at the N-terminus.

The reagents to derivatise amines and carboxyls are also simpler than those necessary for the coupling agents used in sequencing reactions.

Immobilisation Agents

It is possible to capture derivatised peptides with a variety of chemical agents. In the discussion of the methods of this invention biotin has been chosen as an exemplary immobilisatioin agent due to its highly specific interactions with avidin. Other immobilisation agents besides biotin are compatible with the methods of this invention. The following are examples and the invention is not limited to these.

A linker to hexahistidine would allow peptide tags to be captured onto a coordinated metal ion derivatized column. Various antibody antigen interactions could be used as well where an antibody or antigen is tagged onto the penultimate amino acid rather than biotin.

Antibodies against derivatives:

The most common N-terminal modification is acetylation. It should be possible to raise an antibody against N-terminally acetylated peptides to permit these to be captured using an affinity column derivatized with such an antibody. In order to capture substantially al proteins one can derivatize the remaining proteins in a sample, that are not already acetylated, with an acetylation agent. The derivatized proteins can then be cleaved with chymotrypsin or another sequence specific agent (trypsin does not cleave acetylated cleavage sites of proteins). An anti-N-terminal acetylation antibody immobilised on an appropriate matrix could be used to generate an affinity column. Such a column could be used to capture peptide signatures with acetylated N-termini after their source proteins have been cleaved.

To capture C-terminal peptides one could raise an antibody against thiohydantoin derivatives of peptides which could be used to selectively capture a peptide from a protein that had been derivatised with a coupling agent for sequencing prior to cleavage with trypsin or another sequence specific cleavage agent.

Derivitisation of proteins:

The methods of this invention include derivitization steps which are required to ensure that the reference terminus of each protein in a population is specifically derivatised with an immobilisation agent in the first format of, in the second format, to ensure that the reference terminus is specifically blocked from reaction with an immobilisation agent. Additional derivitization steps may also be performed. These may be desirable if fractionation of signature peptides is to be performed prior to mass spectrometry analysis. There are two important factors that should be considered with regard to any fractionation steps. These factors are the resolution of the fractionation step and the consequent sample loss imposed by the fractionation.

Certain chromatographic techniques are 'sticky' when used for the separation of peptides, that is to say a proportion of the sample is retained on the separation matrix. It is possible to reduce sample loss of this kind by derivitizing the groups that are involved in adhesion to the separation matrix. That is to say, if one is using an ion exchange chromatography separation one can derivatize ionic and polar side chains with reagents that increase their hydrophobicity thus reducing affinity to the matrix. This will however, reduce the resolution of the separation.

It is desirable to ensure that only one mass peak per peptide appears in the mass spectrum generated by analysis of a population of signature peptides. It may, therefore, be desirable to derivatise polar and ionic side chains of signature peptides in order to reduce the number of ionization states accessible to those peptides. This step should help promote the formation of a single ion species per signature peptide.

It may also be desirable to add a group to each signature peptide to increase the sensitivity of the mass spectrometry analysis. A particularly good 'sensitizing' group to add to a peptide would be a tertiary ammonium ion which is a positively charged entity with excellent detection properties.

Pre-Sorting Steps:

This technology can be used to profile peptide populations generated in numerous ways. Various fractionation techniques exist to sub-sort proteins on the basis of certain features. Of particular interest is the analysis of signaling pathways. Phosphorylation of proteins by kinases is a feature of many signalling pathways. Proteins that can be phosphorylated by a kinase often have a short phosphorylation motif that a kinase recognizes. Antibodies exist that bind to such motifs, some binding phosphorylated forms while others bind the non-phosphorylated state. Antibody affinity columns or immuno-precipitation of kinase target sub-populations followed by profiling would be of great interest in identifying these proteins and in monitoring their metabolism simultaneously in time resolved studies of live model systems.

Many proteins exists as complexes and analysis of such complexes is often tricky. A cloned protein that is a putative member of a complex allows one to generate an affinity column with that protein to trap other proteins that bind to it. This profiling technology is eminently suited to analysis of such captured protein complexes.

Kits including antibody affinity columns to analyse signal transduction or membrane location by capturing proteins with the appropriate post-translational modifications are envisaged either as a pre-sorting step or as a capture step after cleavage of a protein population with a sequence specific cleavage agent.

Chromatographic techniques:

having generated peptide tags from a population of proteins it is then desirable to analyse the resultant tags. Chromatography is an optional step in the analysis of a population of peptide signatures prior to mass spectrometry but may be quite desirable depending on the configuration of the mass spectrometer used.

Two important features are required of any chromatographic stage in a protein profiling method, high resolution and minimal sample loss. Resolution generates information and also reduces the complexity of the peptide tag population entering the mass spectrometer. The second feature is that there is minimal loss of sample in the chromatographic separation, that would reduce the sensitivity of the technique to low frequency peptides in the population under analysis.

Derivitisation of proteins:

Certain chromatographic techniques are 'sticky' when used for the separation of peptides, that is to say a proportion of the sample is retained on the separation matrix. To reduce sample loss of this kind is possible by derivitizing the groups that are involved in adhesion to the separation matrix. That is to say, if one is using an ion exchange chromatography separation one can derivitise ionic and polar side chains with reagents that increase their hydrophobicity thus reducing affinity to the matrix. This feature needs to be balanced against the need for resolution though.

The use of the C-terminal sequencing agents to derivitise the free carboxyl groups which will reduce the adhesion between such peptides and a cation exchange resin. This may mean that cation exchange chromatography may be advantageous as a chromatographic separation step.

One can derivities quite readily acetylate amine residues to achieve similar effects for anion exchange chromatography.

Analysis of Peptides by mass Spectrometry
Ionisation Techniques:

In general peptide mixtures are injected into the mass spectrometer by electrospray or MALDI TOF, which leaves them in the vapour phase.

Electrospray Ionisation:

Electrospray ionization requires that the dilute solution of biomolecule be 'atomized' into the spectrometer from an insertion probe, i.e. in a fine spray. The solution is, for example, sprayed from the tip of a needle in an electrostatic field gradient. The mechanism of ionization is not fully understood but it through to work broadly as follows. The electrostatic field charges droplets formed at the probe tip promoting atomization. In the stream of nitrogen the solvent is evaporated. With a small droplet, this results in concentration of the biomolecule. Given that most biomolecules have a net charge this increase the electrostatic repulsion of the dissolved protein. As evaporation continues this repulsion ultimately becomes greater than the surface tension of the droplet and the droplet 'explodes' into smaller droplets. The electrostatic field helps to further overcome the surface tension of the charged droplets. The evaporation continues from the smaller droplets which, in turn, explode iteratively until essentially the biomolecules are in the vapour phase, as is all the solvent.

Atmospheric Pressure Chemical Ionization:

An ionization technique appropriate for use the LCMS, for analysing peptides is Atmospheric Pressure Chemical Ionisation (APCI). This is an electrospray based technique where the ionisation chamber is modified to include a discharge electrode which can be used to ionize the bath gas which in turn will collide with the vaporized sample molecules increasing ionization of the sample.

Fast Atom Bombardment:

This is an ionisation technique that is quite similar to APCI and is highly compatible with samples in solution. Typically, a continuous flow of liquid from a capillary electrophoresis column or an HPLC column can be pumped through an insertion probe to a hole or a frit at its tip where the solution is bombarbed by accelerated atoms or ions, usually of xenon or caesium. Collision with the dissolved sample results in transfer of kinetic energy to and ionization of the sample.

Matrix Assisted Laser Desorption Ionization (MALDI):

MALDI requires that the biomolecule solution be embedded in a large molar excess of an photo-excitable 'matrix'. The application of laser light of the appropriate frequency (266 nm beam for nicotinic acid) results in the excitation of the matrix which in turn leads to excitation and ionization of the embedded biomolecule. This technique imparts a significant quantity of translational energy to ions, but tends not to induce excessive fragmentation despite this. Accelerating voltages can again be used to control fragmentation with this technique though.

MALDI techniques can be supported in two ways. One can proteins in a MALDI matrix, where the proteins themselves are not specifically excitable by laser or one can construct peptide labels that contain the necessary groups to allow laser energization. The latter approach means the labels do not need to be embedded in a matrix before performing mass spectrometry. Such groups include nicotinic, sinapinic or cinnamic acid moieties. MALDI based cleavage of labels would probably be most effective with a photocleavable linker as this would avoid a cleavage step prior to performing MALDI mass spectrometry. The various excitable ionization agents have different excitation frequencies so that a different frequency can be chosen to trigger ionization from that used to cleave the photolysable linker. These excitable moieties are easily derivitised using standard synthetic techniques in organic chemistry so labels with multiple masses can be constructed in a combinatorial manner.

All of the above techniques are routinely used with peptides and proteins and are preferred methods of ionization with this invention.

Mass Spectrometric Sensitivity and Quantitation of Peptide Tags

The end result is then that a population of proteins can be arbtitrarily sorted into populations of peptides of convenient size to be fed into a mass spectrometer for analysis. Completion of such an analysis for an entire cell's proteins would give a profile of what proteins are present and in what relative quantities. Absolute quantitation could be achieved by 'spiking' a protein population with known quantities of particular proteins, known to be absent, e.g. plant proteins in animal samples or visa versa, against which to calibrate results. Internal quantities can be determined by measuring relative quantities of certain proteins present at relatively fixed concentrations in most cells such as histones. Various techniques coupled to certain mass spectrometer geometries permit good quantitation with a mass spectrometer. These issues are dealt with fully in GB 9719284.3.

Mass Analyser Geometries

Mass spectrometry is a highly diverse discipline and numerous mass analyzer configurations exist and which can often be combined in a variety of geometries to permit analysis of complex organic molecules such as the peptide tags generated with this invention.

Accurate Mass Measurement

Double focussing mass spectrometers are capable of measuring molecular masses to a very high accuracy, i.e. fractions of a dalton. This permits one to distinguish molecules with identical integer mass but different atomic compositions with ease as fractional differences in the mass of different atomic isotopes allow such distinctions. For determining the molecular masses of a population of peptide tags, this technique may be very effective as it would allow identification of a significant proportion of peptides without requiring any sequencing even if some do have the same integral mass. The few ambiguous peptides that remain could be analysed by tandem mass spectrometry as discussed below.

Sequencing of peptide tags of Tandem mass spectrometry:

Peptides can be readily sequenced by tandem mass spectrometry. Tandem mass spectrometry describes a number of techniques in which a ions from a sample are selected by a first mass analyzer on the basis of their mass charge ratio for further analysis by induced fragmentation of those selected ions. The fragmentation products are analysed by a second mass analyzer. The first mass analyser in a tandem instrument acts as a filter selecting ions to enter the second mass analyser on the basis of their mass charge ratio, such that essentially a species of only a single mass/charge ratio, usually only a single peptide ion, enter the second mass analyser at a time. On leaving the first mass analyzer, the selected peptide passes through a collision chamber, which results in fragmentation of the peptide. Since fragmentation occurs mostly at the peptide bond, the pattern of fragments corresponds to a series of subspecies of peptides and amino acids that compose the original peptide. The distinct pattern of masses of single amino acids, 2-mers, 3-mers, etc. generated in the fragmentation of a peptide is sufficient to identify its sequence.

ION SOURCE→COLLISION CELL→MS2→ION DETECTOR

Various tandem geometries are possible. Conventional 'sector' instruments can be used where the electric sector provide the first mass analyzer stage, the magnetic sector provides the second mass analyser, with a collision cell placed between the two sectors. This geometry is not ideal for peptide sequencing. Two complete sector mass analyzers separated by a collision cell could be used for peptide sequencing. A more typical geometry used is a triple quadrupole where the first quadrupole filters ions for collision. The second quadrupole in a triple quadrupole acts as a collision chamber while the final quadrupole analyses the fragmentation products. This geometry is quite favorable. Another more favorable geometry is a Quadrupole/Orthogonal Time of Flight tandem instrument where the high scanning rate of a quadrupole is couple to the greater sensitivity of a TOF mass analyser to identify the products of fragmentation.

Sequencing with Ion Traps:

Ion Trap mass spectrometers are a relative of the quadrupole spectrometer. The ion trap generally has a 3 electrode construction—a cylindrical electrode with 'cap' electrodes at each end forming a cavity. A sinusoidal radio frequency potential is applied to the cylindrical electrode while the cap electrodes are biased with DC or AC potential. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath gas', such as helium, present in the ion trap cavity. This increases both the resolution and the sensitivity of the device by collision with trapped ions. Collisions both increase ionisation when a sample is introduced into the trap and damp the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving a narrower larger peaks.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. One can retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

For the purposes of protein profiling a peptide population, an ion trap is quite a good instrument. A sample of peptide tags can be injected into the spectrometer. Peptide tags that are expected to appear in a profile, such as housekeeping proteins or histone peptides from eukaryote cell samples, can be ejected specifically and quantified rapidly. The remaining peptides can be scanned. Totally new peptides can then be selectively retained from subsequent samples of the peptide population and can be induced to fragment allowing sequence data for the peptide to be acquired. Alternatively an Ion Trap can form the first stage of a tandem geometry instrument.

Fourier Transform Ion Cyclotron Resonance Mass Spectrometry (FTICR MS):

FTICR mass spectrometry has similar features to ion traps in that a sample of ions is retained within a cavity but in FTICR MS the ions are trapped in a high vacuum chamber by crossed electric and magnetic fields. The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radiofrequency pulse to two 'transmitter plates' which form two further opposing sides of the box. The cycloidal motion of the ions generate corresponding electric fields in the remaining two opposing sides of the box which comprise the receiver plates'. The excitation pulses excite ions to large orbits which decay as the coherent motions of the ions is lost through collisions. The corresponding signals detected by the receiver plates are converted to a mass spectrum by fourier transform analysis.

For induced fragmentation experiments these instruments can perform in a similar manner to an ion trap—all ions except a single species of interest can be ejected from the trap. A collision gas can be introduced into the trap and fragmentation can be induced. The fragment ions can be subsequently analysed. Generally fragmentation products and bath gas combine to give poor resolution if analysed by FT of signals detected by the 'receiver plates', however the fragment ions can be ejected from the cavity and analyzed in a tandem configuration with a quadrupole, for example.

For protein profiling FTICR MS could be used and may be advantageous as these instruments have a very high mass resolution allowing for accurate mass measurement so that peptides with the same integer mass but different atomic compositions can be resolved. Furthermore unidentified peptide tags can be subsequently analyzed by fragmentation.

Protein Immobilisation

A great deal of knowledge has been accumulated about specific protein chemistries particularly in the area of organic synthesis of peptides.

R. B. Merrifield, Science 232: 341–347, 1986.

S. B. H. Kent, "Chemical Synthesis of Peptides and Proteins", Annu. Rev. Biochem. 1988. 57: 957–989.

Linkers

An important feature of this invention is cleavable linkers to their relevant biomolecules. Photocleavable linkers are particularly desirable as they allow for rapid, reagentless cleavage. For references, see:

Theodora W. Greene, "Protective Groups in Organic Synthesis", 1981, Wiley-Interscience.

On photoremovable groups:

Patchornik, J. Am. Chem. Soc. 92: 6333 -, 1970.

Amit et al, J. Org. Chem. 39: 192 -, 1974.

Liquid Chromatography:

R. Scopes, "Protein Purification: Principles and Practice", Springer-Verlag, 1982.

M. Deutscher, "Guide to Protein Purification", Academic Press, 1990.

Mass Spectrometry:

Electrospray mass spectrometry is the preferred technique for sequencing peptides since it is a very soft technique and can be directly coupled to the liquid phase molecular biology used in this invention. For a full discussion of mass spectrometry techniques see:

K. Biemann, "Mass Spectrometry of Peptides and Proteins", Annu. Rev. Biochem. 1992, 61: 977–1010.

R.A.W. Johnstone and M. E. Rose, "Mass Spectrometry for chemists and biochemists" 2nd edition, Cambridge University Press, 1996.

EXPERIMENT

Outline of Embodiment of Protein Profiling

This comprises a system where (i) a protein has its carboxyl groups protected, the last amino acid removed leaving just one carboxyl group free at the cleaved terminus.

(ii) This will be reacted with a biotinylation reagent, so that the carboxy terminus is labelled with biotin.

(iii) The protein is fragmented with a protease to leave peptide fragments, only the carboxyl one being biotinylated.

The biotin is used to attach the C terminal fragment to immobilised streptavidin, or preferably monomeric avidin, from which it can be released with mild acid and made available for MS—MS.

All reagents are available, and the chemistry is generally well-known as follows:

(i) The technique of carboxy-terminal sequencing of proteins is established. We note that the method of Boyd et al., (Boyd, V L, Bozzini, M, Guga, P J, DeFranco, R J, Yuan, P-M, Loudon, G M and Nguyen, D; J. Org Chem, 60, 2581, (1995)) blocks the side chain carboxyls of aspartate and glutamate residue by amidation during removal of the terminal amino acid.

(ii) Biotinylation of the free carboxyl group at the carboxy terminus may be achieved using 5-(biotimamido) pentylamine/1-ethyl-3-[3-dimethylaminopropyl] carbodiimide hydrochloride, which is marketed by Pierce & Warriner (Lee, K Y, Birckbichler, P J and Patterson, M K, Clin Chem, 34, 906 (1988) for such a purpose.

(iii) Protease fragmentation of proteins on a membrane is an established technique (Sutton, C W, Pemberton, K S, Cottrell, J S, Corbett, J M, Wheeler, C H, Dunn, M J and Pappin, D J, Electrophoresis, 16, 308, (1995), and Millipore Corporation produce Immobilon-CD and other PVDF membranes for that purpose. Monomeric avidin is produced by Pierce and Warriner, and allows release of biotinylated molecules using 2 mM biotin in phosphate buffered saline.

The remaining step in the method is the use of PVDF membranes (as used for trypsinization) in lieu of Zitex membranes for the sequencing reaction (I).

METHODOLOGY

Binding of Lysozyme of PVDF Membrane 0.5 mm squared pieces of PVDF (Millipore) were wetted with isopropanol and incubated in 20 mg/ml lysozyme (Pharmacia) in PBS at room temperature for 30 minutes. The membranes were then air dried and stored at 4° C. until used.

Modification (Carboxyl Group Protection) of Lysozyme Bound to PVDF.

Modification solution was prepared by mixing 62 mg of 2-ethyl-5-phenylisoxazolium-3'-sulfonate (Aldrich) with 50 ul of diisopropylethylamine (Aldrich) in 2 mls of $CH_3CN$ 100 ul of modification solution was added to each membrane and incubated at room temperature for 4 hours.

Following incubation 900 ul of water was added and each membrane was gently shaken at room temperature for 30 minutes. Each membrane was then transferred to 50 ul of $CH_3CN$, 450 ul of water was added and the membranes were gently shaken at room temperature for 30 minutes.

The each membrane was then transferred to 500 ul of 2% trifluoroacetic acid and incubated at room temperature overnight.

Trypsin Digest

Each membrane was transferred to 250 ul of 25 mM ammonium bicarbonate pH7.6 solution and gently shaken at room temperature for 15 minutes.

Each protein/protein containing membrane was added/transferred to 200 ul of ammonium bicarbonate solution pH7.6 containing 5 ug of trypsin and incubated at 37° C. overnight.

Eluation of Protein/Peptide Fragments From Membrane

Each membrane was transferred to 100 ul of 50% formic acid/50% ethanol solution and incubated at room temperature for 30 minutes to remove the protein/peptides. The membranes were then removed and 300 ul of water added to the 50% formic acid/50% ethanol solution containing the protein/peptides.

Analysis

The following were analyzed by reversed phase HPLD.

40 ug of trypsin in PBS; 40 ug of lysozyme in PBS; 40 ug of lysozyme digested with trypsin; 40 ug of trypsin digested with trypsin; membrane bound modified lysozyme digested with trypsin; membrane put through the modification protocol without lysozyme and digested with trypsin; membrane bound lysozyme unmodified and digested with trypsin; membrane bound lysozyme modified without trypsin digestion.

Results

We have now performed the operation using PVDF membranes in lieu of Zitex membranes for the sequencing reaction (I). We have found that the reversed phase HPLC chromatogram for lysozyme (used as a typical protein) obtained after treatment with the sequencing reactions on a PVDF membrane and trypsinization, from which the chromatogram for the same process in the absence of lysozyme has been subtracted, is similar to that obtained for lysozyme trypsinized directly. Hence the technologies are compatible and can be used to generate 'signature' peptides for MS—MS identification (data not shown).

KEY TO THE DRAWINGS

Figure 1B:
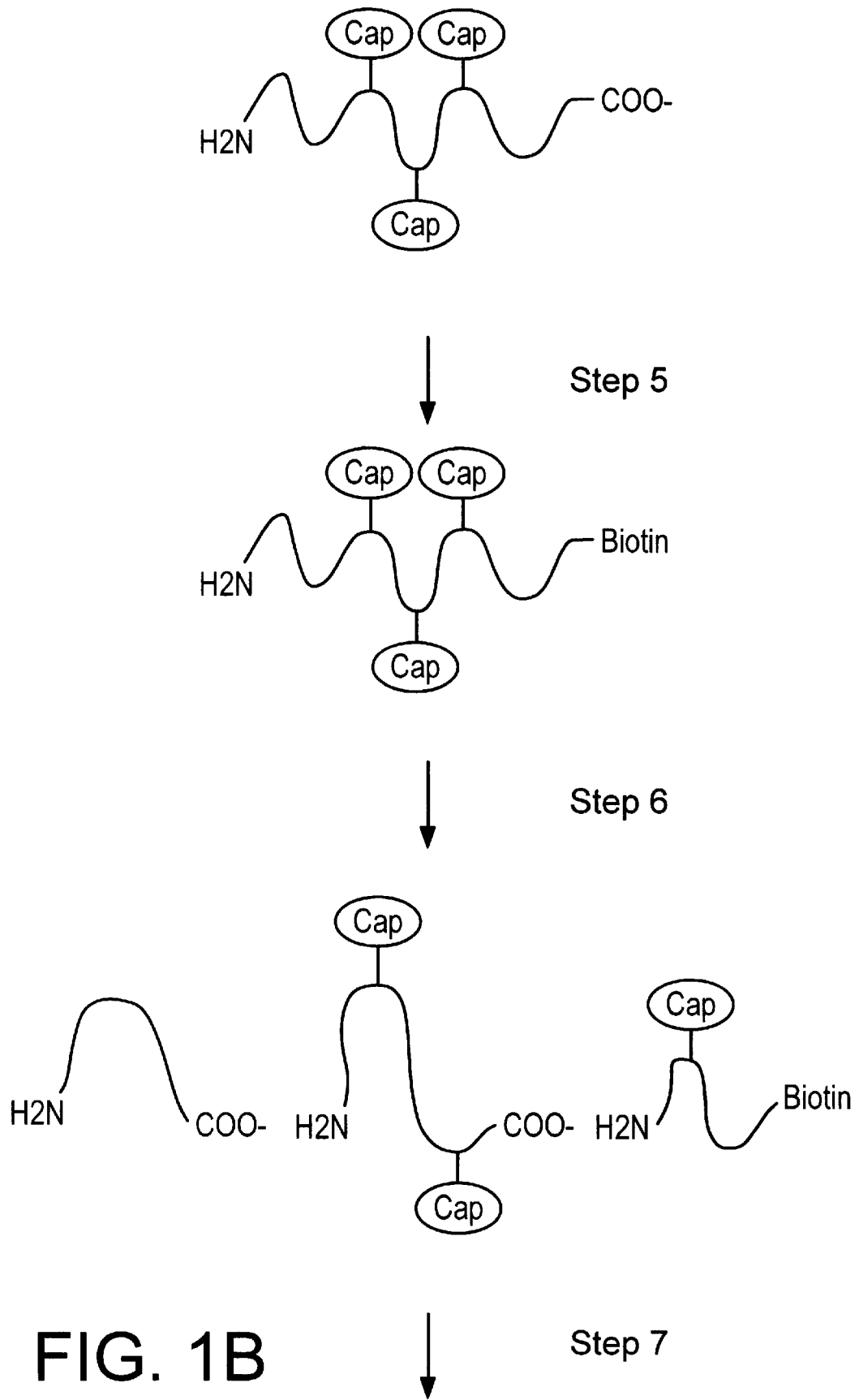
Figure 1C:
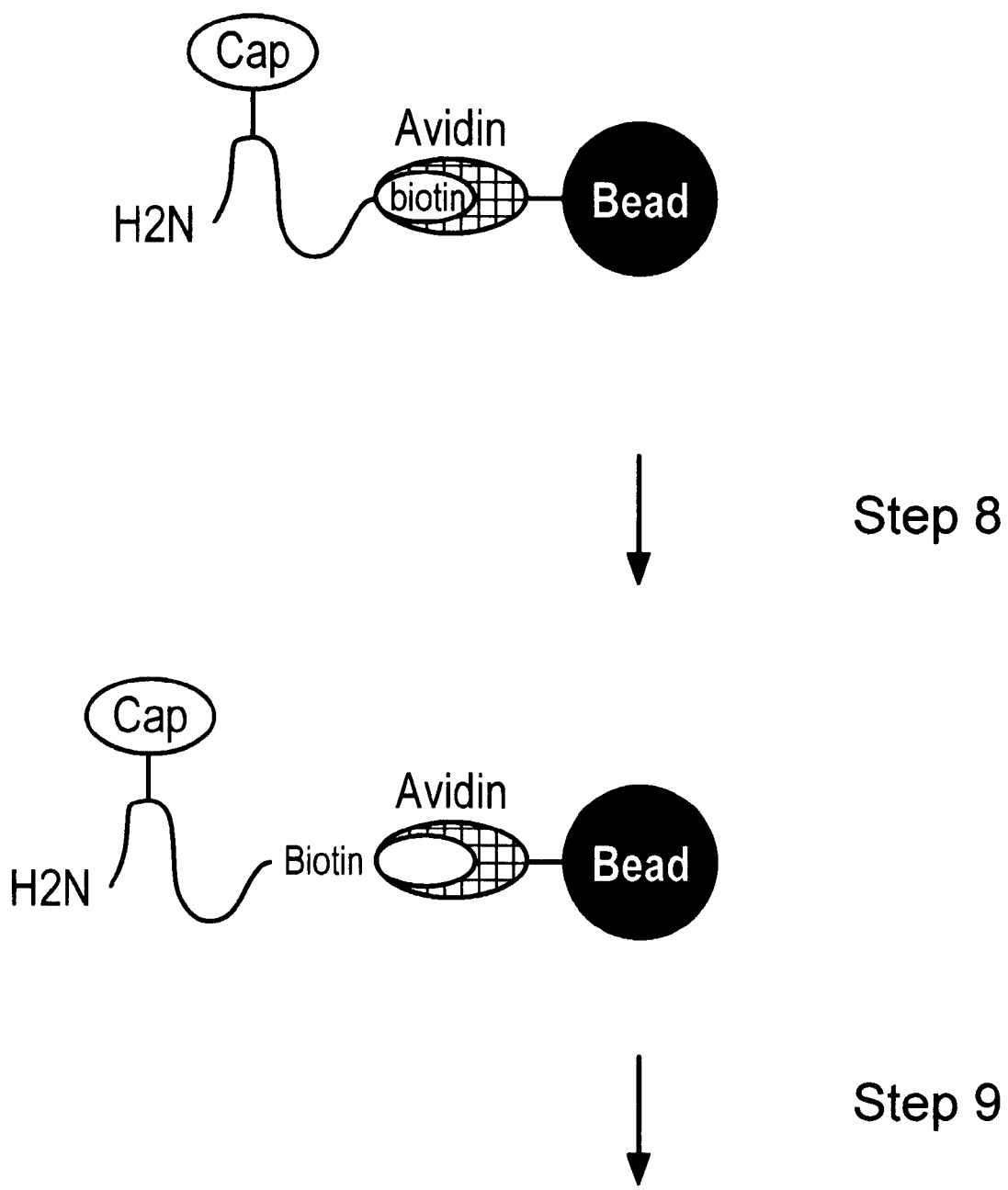
Figure 2A:
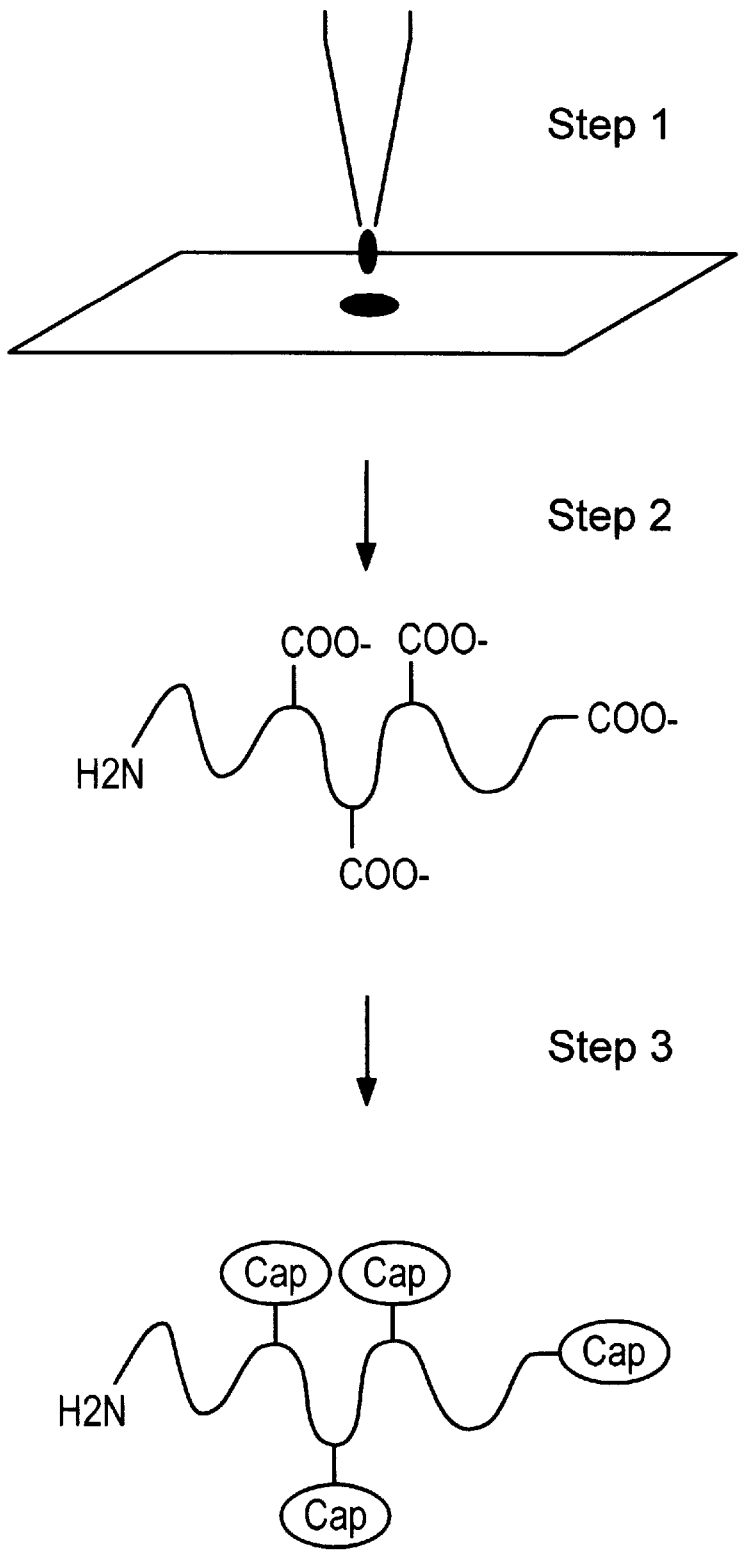
FIGS. 2A-2C shows a reaction scheme according to another embodiment of the invention.
Figure 2B:
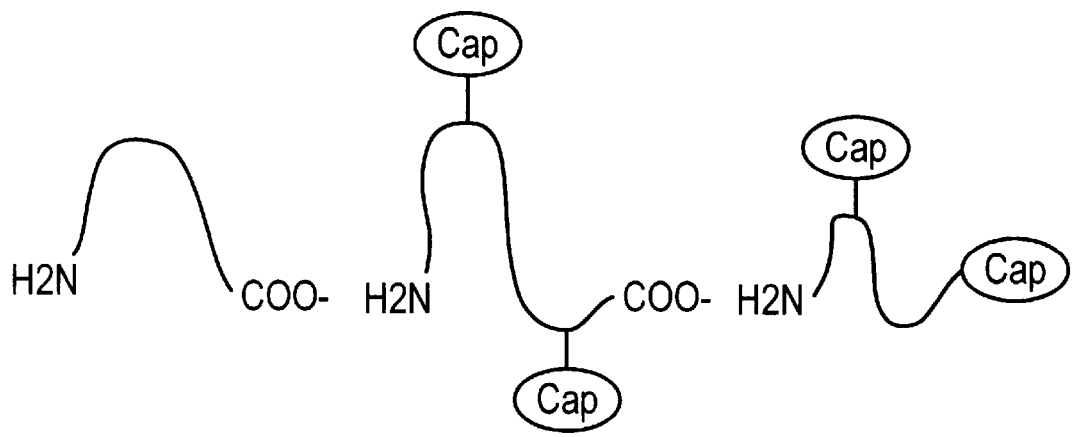
Figure 2B:
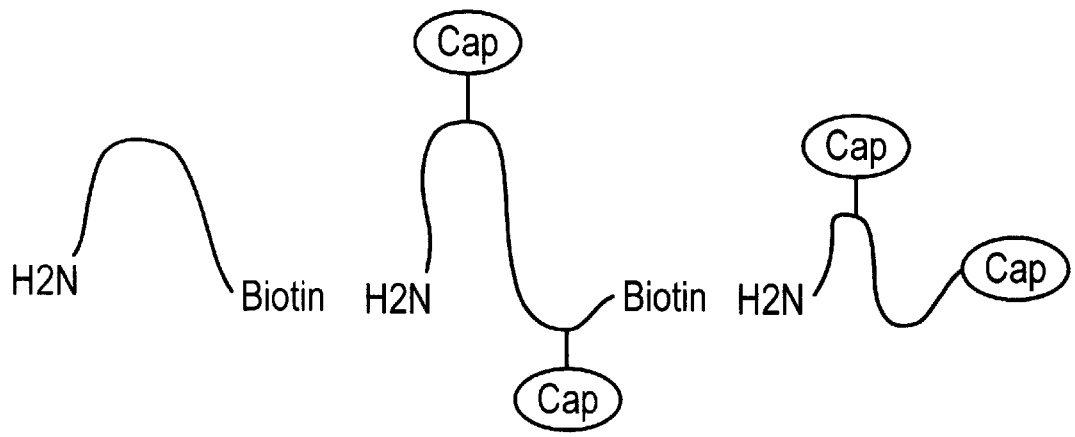
Figure 2C:
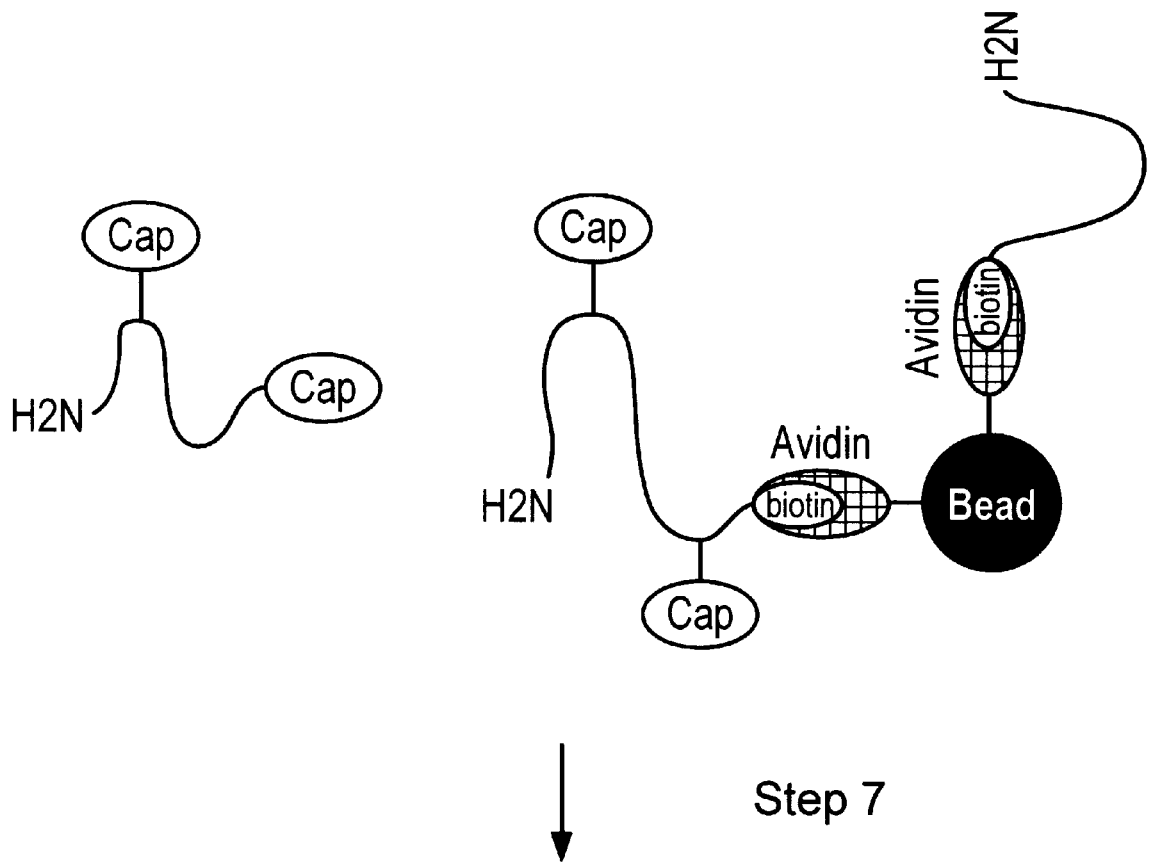

FIGS. 1A-1C
Step 1: Extract proteins with harsh solvents and capture extracted proteins onto a PVDF membrane
Step 2: Loosely immobilized proteins can be washed to dispose of harsh solvents
Step 3: Treat proteins with C-terminal coupling agent
Step 4: Treat derivitized proteins with cyclisation reagent and then cleave terminal amino acid from derivitised protein
Step 5: Biotinylate newly exposed penultimate amino acid carboxyl group
Step 6: Wash membrane bound proteins to remove chemical agents and cleave proteins with trypsin in physiological buffer
Step 7: Capture terminal fragments onto avidinated beads
Step 8: Wash away free peptides then release captured peptide 'tags' for analysis
Step 9: Analyse by MS or LC/MS/MS or MS/MS FIGS. 2A-2C
Step 1: Extract proteins with harsh solvents and capture extracted proteins onto a PVDF membrane
Step 2: Loosely immobilized proteins can be washed to dispose of harsh solvents
Step 3: Treat proteins with C-terminal coupling agent
Step 4: Wash membrane bound proteins to remove chemical agents and cleave proteins with trypsin or other sequence specific cleavage agent in in physiological buffer
Step 5: Biotinylate newly exposed carboxyl termini
Step 6: Capture terminal fragments onto avidinated beads in an affinity column of example
Step 7: Analyse elute C-terminal by MS or LC/MS/MS or MS/MS FIGS. 3A-3B
Step 1: Extract proteins with harsh solvents and capture extracted proteins onto a PVDF membrane
Step 2: Loosely immobilized proteins can be washed to dispose of harsh solvents
Step 3: Treat proteins with C-terminal coupling agent carrying immobilization effector
Step 4: Wash membrane bound proteins to remove chemical agents and cleave proteins with trypsin in physiological buffer
Step 5: Capture terminal fragments onto avidinated beads
Step 6: Wash away free peptides then release captured peptide 'tags' for analysis
Step 7: Analyse by MS or LC/MS/MS or MS/MS FIGS. 4A-4C
Step 1: Extract proteins with harsh solvents and capture extracted proteins onto a PVDF membrane
Step 2: Loosely immobilized proteins can be washed to dispose of harsh solvents
Step 3: Treat proteins with C-terminal coupling agent
Step 4: Treat coupled proteins with derivitisation reagent to ensure all exposed carboxyls are capped
Step 5: Treat derivitized proteins with cyclisation reagent and then cleave terminal amino acid from derivitised protein
Step 6: Biotinylate newly exposed penultimate amino acid carboxyl group
Step 7: Wash membrane bound proteins to remove chemical agents and cleave proteins with trypsin in physiological buffer
Step 8: Capture terminal fragments onto avidinated beads
Step 9: Wash away free peptides then release captured peptide 'tags' for analysis
Step 10: Analyse by MS or LC/MS/MS or MS/MS

What is claimed is:

1. A method for characterizing polypeptides, which comprises:

(a) treating a sample comprising a population of a plurality of polypeptides with a cleavage agent which is known to recognize in polypeptide chains a specific amino acid residue or sequence and to cleave at a cleavage site, whereby the population is cleaved to generate peptide fragments;

(b) isolating a population of peptide fragments which comprises only terminal peptide fragments bearing as a reference terminus the N-terminus or the C-terminus of the polypeptide from which fragments were derived, each peptide fragment bearing at the other end the cleavage site proximal to the reference terminus; and (c) determining by mass spectrometry a signature sequence of at least some of the isolated fragments, which signature sequence is the sequence of a predetermined number of amino acid residues running from the cleavage site;

wherein a signature sequence characterize each polypeptide.

2. The method according to claim 1, wherein the reference terminus is attached to a solid phase support to immobilized the population of polypeptides or peptide fragments thereof.

3. The method according to claim 2, wherein the population of polypeptides is immobilized before treatment with the cleavage agent.

4. The method according to claim 2 or claim 3, wherein the reference terminus is attached to the solid phase support by: (i) treating the polypeptides with a blocking agent to block all exposed reference groups, which comprise either carboxyl groups or primary amine groups; (ii) cleaving the reference terminal amino acids to expose unblocked reference termini; and iii) treating the unblocked reference termini with an immobilisation agent capable of coupling to the solid phase support; wherein step (b) comprises binding the treated reference termini to the solid phase support and removing unbound peptide fragments.

5. The method according to claim 1, which further comprises (i) preparing the sample step (a) by pre-treating the polypeptides with a blocking agent to block all exposed reference groups, which comprise either carboxyl groups or primary amine groups, so that subsequent treatment of the sample with the cleavage agent generates peptide fragments bearing unblocked reference termini;

(ii) treating the unblocked reference termini with an immobilization agent capable of coupling to a solid phase support; and (iii) binding the peptide fragments containing the unblocked reference termini to the solid phase support; wherein step (b) comprises eluting unbound peptide fragments therefrom.

6. The method according to claim 4, wherein the immobilization agent comprises a biotinylation agent.

7. The method according to claim 4, wherein the reference group is carboxyl.

8. The method according to claim 1, wherein the cleavage agent comprises a peptidase.

9. The method according to claim 1, wherein the sample of step (a) comprises a sub-cellular fraction.

10. The method according to claim 1, which further comprises preparing the sample of step (a) by liquid chromatography.

11. The method according to claim 1, wherein the mass spectrometry is preceded by a high pressure liquid chromatography step to resolve the peptide fragments.

12. The method according to claim 1, wherein the peptide fragments are subjected to ion exchange chromatography before step (c).

13. The method according to claim 1, wherein the predetermined number of amino acid residues is from 3 to 30.

14. A method for identifying polypeptides in a test sample, which comprises characterizing the polypeptides in accordance with a method according to claim 1, comparing the signature sequences and relative positions of the cleavage site obtained thereby with the signature sequences and relative positions of the cleavage site of further polypeptides in order to identify the or each polypeptide in the test sample.

15. A method for assaying for one or more specific polypeptides in a test sample, which comprises performing a method according to claim 1, wherein the cleavage agent and relative position of the cleavage site is predetermined and the signature sequence is determined in step (c) by assaying for a predetermined sequence of amino acid residues running from the cleavage site.

16. A method according to claim 15, wherein the cleavage site and signature sequence are predetermined by selecting corresponding sequences from one or more known target polypeptides.

* * * * *